United States Patent
Blumentritt et al.

(10) Patent No.: US 7,107,832 B2
(45) Date of Patent: Sep. 19, 2006

(54) MEASUREMENT DEVICE WITH A SUPPORT PLATE MOUNTED ON MEASUREMENT CELLS AND INTENDED FOR A PERSON TO STAND ON

(75) Inventors: Siegmar Blumentritt, Bösinghausen (DE); Walter Hollaschke, Duderstadt (DE); Karl-Heinz Klingebiel, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 307 days.

(21) Appl. No.: 10/792,275

(22) Filed: Mar. 4, 2004

(65) Prior Publication Data
US 2004/0238234 A1    Dec. 2, 2004

(30) Foreign Application Priority Data
Mar. 4, 2003   (DE) ................................ 103 09 567

(51) Int. Cl.
*A61B 5/00*   (2006.01)
*G01G 19/00*  (2006.01)

(52) U.S. Cl. .................. 73/172; 600/587; 600/592; 177/200

(58) Field of Classification Search ........ 177/199–200; 600/587, 592; 73/172
See application file for complete search history.

(56) References Cited

U.S. PATENT DOCUMENTS

| | | | | |
|---|---|---|---|---|
| 1,805,841 A | * | 5/1931 | Nilson | 254/68 |
| 2,653,475 A | * | 9/1953 | Kraus | 73/172 |
| 3,616,690 A | * | 11/1971 | Harden | 73/172 |
| 4,014,398 A | * | 3/1977 | Gresko | 600/592 |
| 4,749,169 A | * | 6/1988 | Pickles | 254/122 |
| 4,986,802 A | * | 1/1991 | Scoville et al. | 475/346 |
| 5,165,660 A | * | 11/1992 | Engel et al. | 254/126 |
| 5,609,162 A | | 3/1997 | Blumentritt et al. | 600/587 |
| 5,750,937 A | * | 5/1998 | Johnson et al. | 177/25.11 |
| 6,437,257 B1 | * | 8/2002 | Yoshida | 177/199 |

FOREIGN PATENT DOCUMENTS

| | | |
|---|---|---|
| EP | 0 663 181 | 7/1995 |
| FR | 2 802 795 | 6/2001 |

OTHER PUBLICATIONS

PTO 06-2521, Feb. 2006.*

* cited by examiner

*Primary Examiner*—Randy W. Gibson
(74) *Attorney, Agent, or Firm*—Whitham, Curtis, Christofferson & Cook, PC

(57) ABSTRACT

A measurement device with a support plate (1) mounted on measurement cells, and with a display device for displaying a force action line (7) for a person standing on bearing surfaces (10, 10') of the support plate (1), permits monitoring of the force action line during a correction or optimization of the position of the person standing on the support plate (1) by virtue of the fact that lifting devices (9) are arranged underneath the bearing surfaces (10, 10') and above the support plate (1).

17 Claims, 5 Drawing Sheets

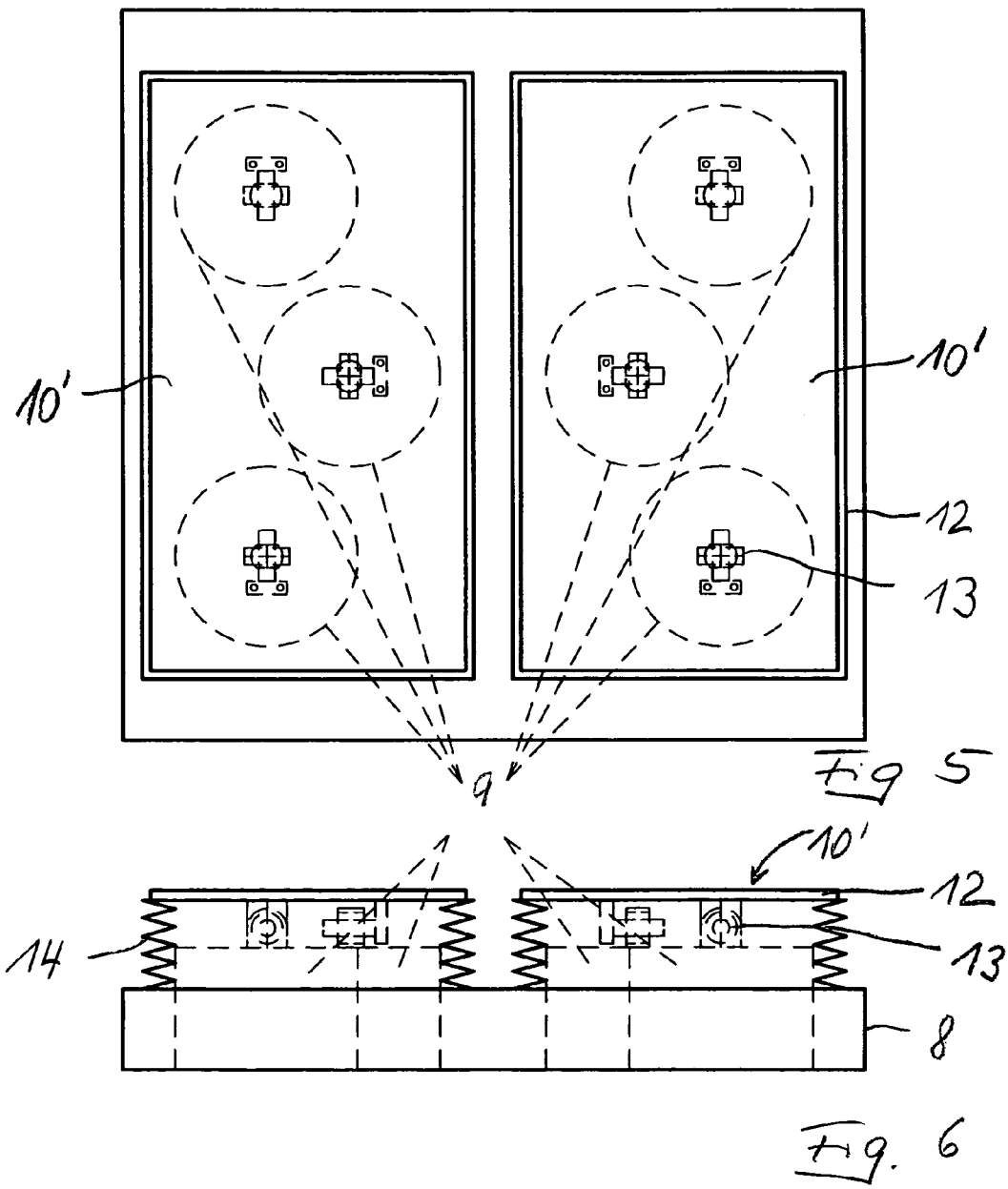

Figure 1:
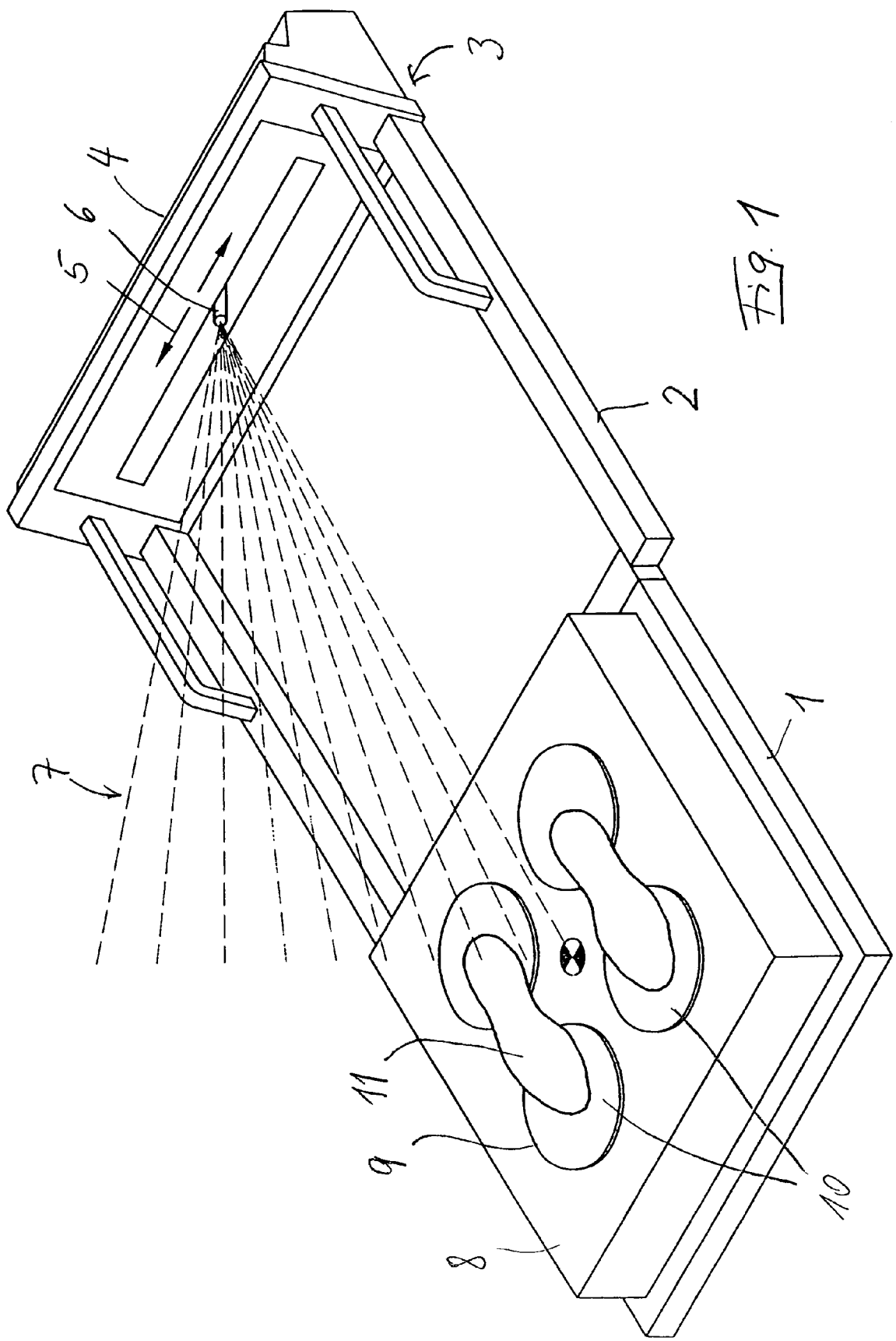

MEASUREMENT DEVICE WITH A SUPPORT PLATE MOUNTED ON MEASUREMENT CELLS AND INTENDED FOR A PERSON TO STAND ON

The invention relates to a measurement device with a support plate mounted on measurement cells and intended for a person to stand on, and with a display device for displaying a force action line for a person standing on bearing surfaces of the support plate.

Poor orthopedic positioning caused by the lower extremities is usually corrected by observation of the geometry of the body. For example, a difference in leg length is assessed on the basis of the position of the pelvis and the course of the lumbar spine. This assessment provides only a rough qualitative finding and in addition cannot be done without risk of error. Possible corrective measures are determined, for example for leg length compensation, using height compensation panels with which the effect of any corrective measures is determined by examining the position of the pelvis and/or the course of the spinal column.

A measurement device of the abovementioned type, and permitting quantitative measurements, has been disclosed by EP 0 663 181 A1. By means of pressure or force sensors arranged, for example, under the corners of a rectangular support plate, a force action line is determined and displayed in the known measurement device, for example by means of the fact that the course of a plane of the center of gravity onto the body of the person standing on the support plate, or the course of a force action line on a leg provided with a prosthesis, is projected by means of a vertically oscillating laser beam. A measurement device of this type is suitable for displaying the course of the plane of the center of gravity both in respect of the frontal plane and also in respect of the sagittal plane of the person standing on the support plate. The known measurement device is used to adapt prostheses or orthotic devices of the lower extremities.

The known measurement device permits an objective assessment of the force pattern of the support apparatus of a human body and in particular a practical adaptation of prostheses or orthotic devices. The effect of corrective measures or of optimization measures is checked by carrying out a renewed measurement after the corrective measure or optimization measure has been performed. However, this procedure can take a considerable amount of time.

It is therefore an object of the present invention to design a measurement device of the type mentioned at the outset in such a way that it is possible to perform improved and simplified corrective or optimization measures.

According to the invention, in order to achieve this object a measurement device of the type mentioned at the outset is distinguished by the fact that lifting devices are arranged underneath the bearing surfaces and above the support plate.

The measurement device according to the invention thus affords the advantage that, by means of the lifting devices, positional corrections can be carried out on the measurement device itself, and it is possible to check the positional corrections immediately in the form of a change in the display value generated by the measurement and shown on the display device. The effect of a positional correction of the person standing on the bearing surfaces is therefore immediately detectable on the basis of the change in the line of the center of gravity shown. In this way, determination of optimal positional corrections is considerably simplified and accelerated. The determination of suitable positional corrections can thus be made objective and is no longer solely dependent on the experience of, for example, an orthopedic engineer, who has hitherto had to determine the degree of correction and optimization on the basis of his experience.

The lifting devices are preferably steplessly adjustable and are preferably designed to be individually adjustable, in particular with an electric adjustment mechanism.

The bearing surfaces are expediently oriented in such a way that they directly support the feet of the person, that is to say are positioned on both sides of a center plane. The center plane can correspond to both the frontal plane and also the sagittal plane of the person standing on the bearing surfaces.

The lifting devices are preferably designed in such a way that it is possible not only to adjust the height of the foot of a person standing on them, but also to vary a bearing angle parallel or transverse to the center plane, so that the effect of in the stance angle variations can also be monitored in the frontal plane or sagittal plane.

It is expedient if the lifting devices for the bearing surfaces are arranged symmetrically with respect to the center plane. In this case, two lifting devices can in each case be provided on both sides of the center plane. A greater variation of the angle settings is made possible by the fact that at least three lifting devices are present on both sides of the center plane.

Taking account of the fact that the measurement device is intended to be suitable especially for disabled persons, for example amputees, it is important that the lifting devices of the measurement device are made as flat as possible, so that disabled persons are also able to step onto the measurement device without any great effort.

A particularly flat configuration of the lifting devices is made possible by the fact that the lifting devices consist of a central hollow spindle screw which is in engagement with at least one rotationally fixed sleeve part having an internal thread cooperating with the spindle screw. The sleeve part can have an end wall which directly forms a part of the bearing surface. The lift generated by the lifting device can be increased still further by the fact that it has upper and lower rotationally fixed sleeve parts which in each case cooperate with oppositely directed external thread portions of the spindle screw.

The spindle screws have a diameter which is greater than 5 cm, preferably greater than 10 cm. It is preferred if a drive mechanism of the spindle screw is formed by a toothed ring arrangement arranged in the inside of the spindle screw and engaging with an internal toothing of the spindle screw. The toothed ring arrangement is preferably configured in the form of a planetary gear. The compact design of the lifting devices also makes it possible to arrange a drive motor of the toothed ring arrangement in the inside of the spindle screw, with the result that an extremely compact measurement device is made available.

In the measurement device according to the invention, the plane of the center of gravity can be displayed by means of a linearly oscillating laser beam or by means of a light beam formed linearly by a suitable lens optical system, in particular a cylindrical lens. The angle of opening of the light beam can therefore be preferably >90°.

Figure 2:
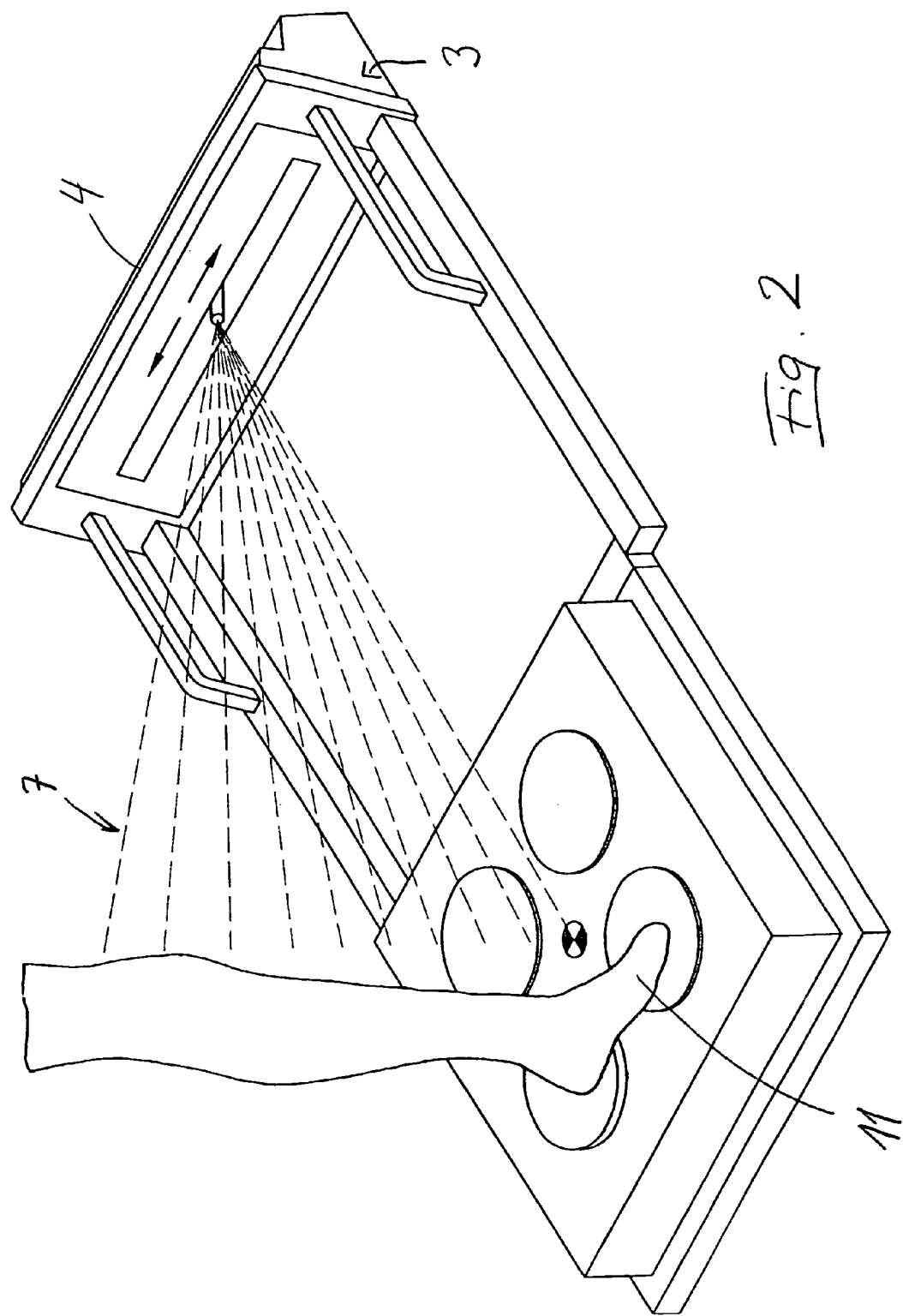
Figure 3:
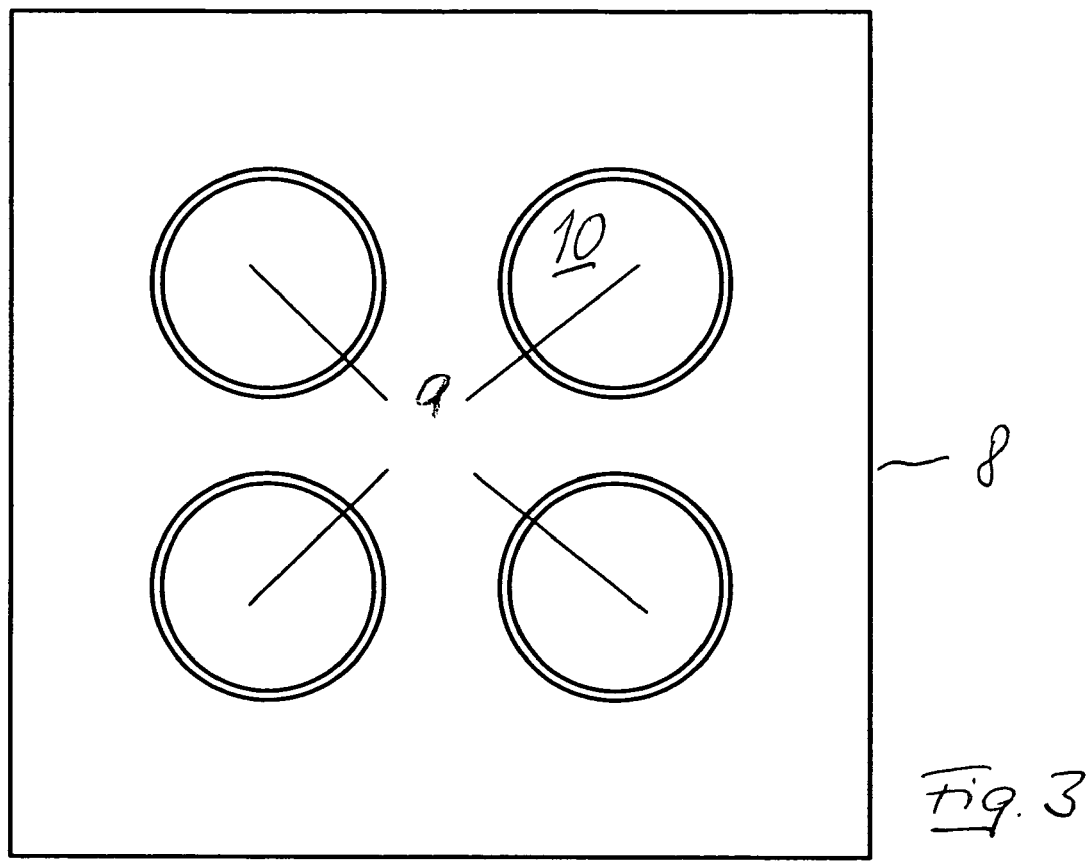
Figure 4:
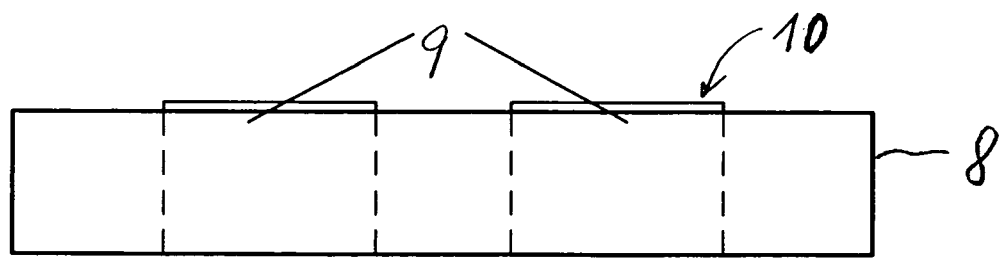
Figure 8:
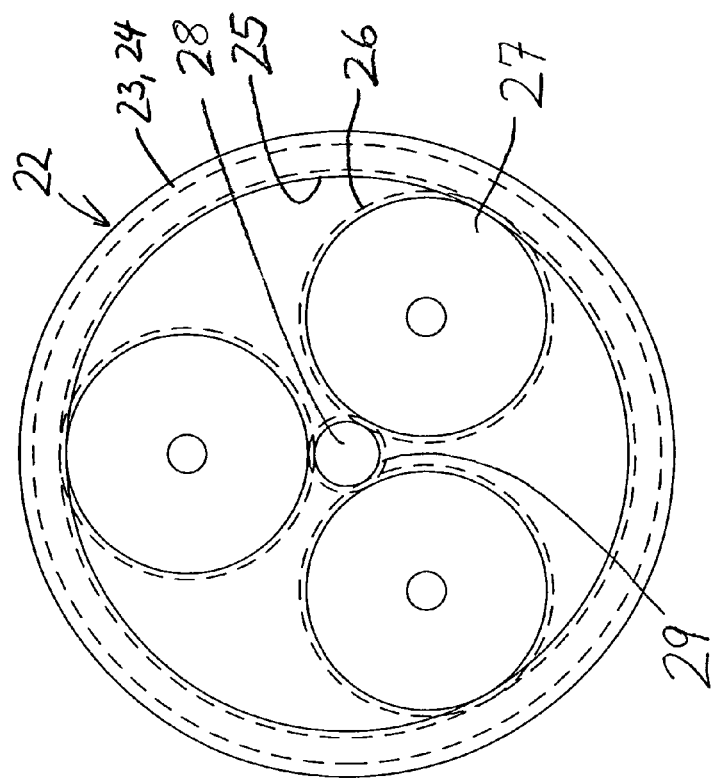
Figure 7:
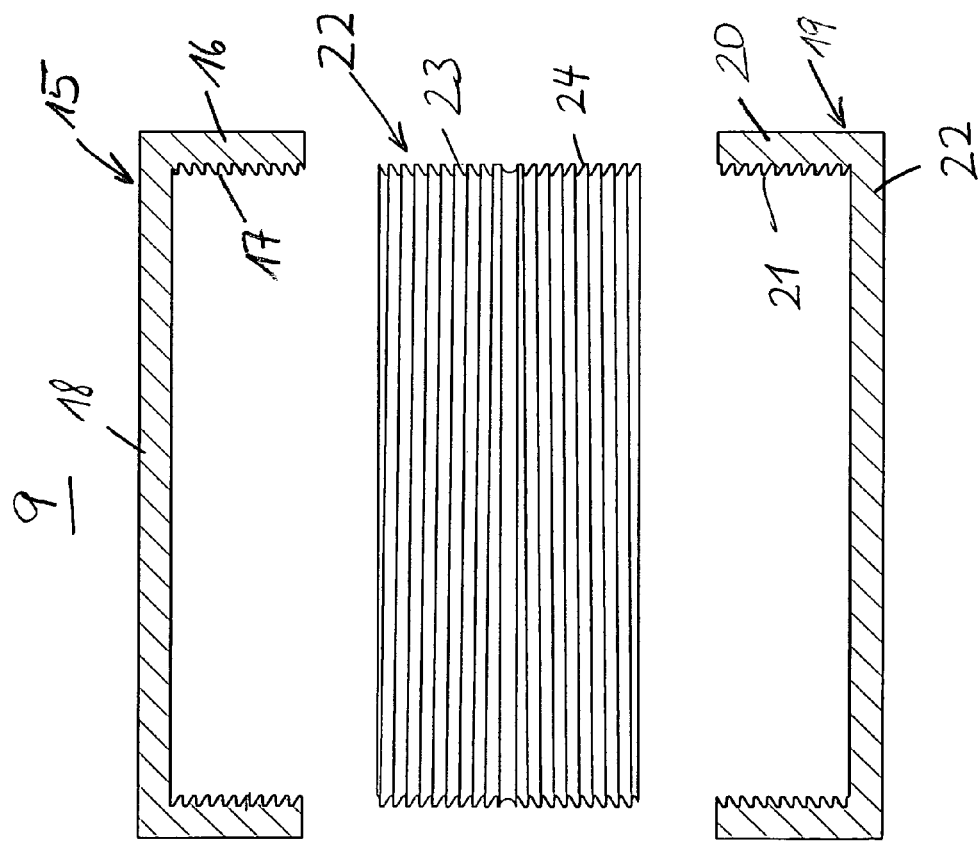

The invention will be explained in greater detail below with reference to illustrative embodiments represented in the drawing, in which:

FIG. 1 shows a diagrammatic representation of an illustrative embodiment of a measurement device according to the invention in an application for determining the frontal statics of the body, FIG. 2 shows the arrangement according to FIG. 1 in the application for determining the statics of the lower extremity in the sagittal plane, FIG. 3 shows a plan view of four column-like lifting devices which form bearing surfaces, FIG. 4 shows a side view of the arrangement according to FIG. 3, FIG. 5 shows a diagrammatic plan view of two bearing surfaces formed by plates, and each with three lifting devices located underneath, FIG. 6 shows a side view of the arrangement according to FIG. 5, FIG. 7 shows a diagrammatic side view of the structure of a preferred lifting device of compact design with a hollow spindle screw, FIG. 8 shows a plan view of the hollow spindle screw according to FIG. 7.

In FIG. 1, a measurement device can be seen which has a rectangular support plate mounted on pressure, force or movement sensors, these being preferably arranged in the corners of the support plate 1. Electrical connections (not shown) running through frame parts 2 of a housing 3 connect the sensors of the support plate 1 to an electronics arrangement in a front closure part 4 of the housing 3. Mounted in the front closure part 4 of the housing 3 there is a carriage which can move laterally in the direction of the indicated arrows 5 and on which a projection optical system 6 is arranged with which a beam of a laser (not shown) can be projected perpendicularly with respect to the front closure part 4 of the housing 3. As is indicated in FIG. 1, the deflector optical system 6 oscillates in the vertical direction, in other words perpendicularly with respect to the surface of the support plate 1 in an angle range of, for example, 30° and thus covers, with an oscillating laser beam 7, a part of a measured plane of the center of gravity. Depending on the measured gravitational force, the carriage 6 moves sideways until the oscillating laser beam 7 is located in the area of the plane of the center of gravity of a person standing on the support plate 1.

Provided above the support plate 1, according to the invention, there is a structure 8 which, according to FIG. 1, comprises four lifting devices 9. The lifting devices 9 are positioned in a quadratic arrangement so that together they form a bearing surface 10 on which a person's feet 11 (indicated diagrammatically) can be placed.

The position of a person's feet 11 is shown in FIG. 1 such that the oscillating laser beam 7 projects a plane of the center of gravity for the frontal statics of the body. By contrast, for the same arrangement represented in FIG. 2, a load is indicated by the foot 11 of a person who is standing sideways with respect to the closure part 4 of the housing 3, so that the oscillating laser beam 7 covers a plane of the center of gravity in the sagittal plane of the person.

In separate views of the structure 8, FIGS. 3 and 4 show the lifting devices 9 which form the bearing surfaces 10 for a person's feet 11.

By contrast, FIGS. 5 and 6 show an embodiment in which bearing surfaces 10' are formed in each case by a rectangular plate 12 which in each case is arranged here above three lifting devices 9. The plate 12 is connected by pivoting hinges 13 to the lifting devices 9 in order to permit tilting of the plates 12, thus leading to a variation in the angle of the bearing surfaces 10'. It will be seen that the plates 12 can be tilted so as to form an angle in the longitudinal direction or a tilting angle of the bearing surface 10' in the transverse direction, or a combination of these. The space between the plate 12 and the structure 8 can expediently be sealed off with a bellows 14.

FIGS. 7 and 8 illustrate a preferred design of the lifting devices 9. According to FIG. 7, these consist of an upper, rotationally fixed sleeve part 15 which has a cylindrical jacket wall 16 with an internal thread 17 and an upper end wall 18. Correspondingly, a lower sleeve part 19 is formed with a cylindrical jacket wall 20 with an internal thread 21 and a lower end wall 22. Both sleeve parts 15, 19 cooperate with a central hollow spindle screw 22 which is provided, along its height, with two oppositely directed external thread portions 23, 24 of identical size. When the two sleeve parts 15, 19 are in engagement with the spindle screw 22, a rotation of the spindle screw 22 in one direction causes the two sleeve parts 15, 19 to move away from a radial center plane of the spindle screw, whereas rotation of the spindle screw 22 in the opposite direction causes the sleeve parts 15, 19 to move in the direction toward the radial center plane. In this way, the two end walls 18, 22 move toward or away from one another. When the lifting device stands on the lower end wall 22, the upper end wall 18 thus moves up or down depending on the rotation of the spindle screw 22.

The drive mechanism of the actual spindle screw 22 is shown diagrammatically in FIG. 8. The spindle screw 22 is of hollow design and has, on its cylindrical inner wall, an internal toothing 25 which engages in the external toothing 26 of three toothed wheels 27 arranged in a star shape. The three toothed wheels 27 are driven by a central drive shaft 28 with external toothing 29. The central drive shaft 28 can be connected directly to an electric motor likewise arranged in the inside of the spindle screw 22 and form the drive shaft of the electric motor.

The design of a lifting device shown in FIGS. 7 and 8 permits a structure 8 with a low height, where the top face of the upper end wall 18 can, according to FIG. 1, directly form the bearing surface 10.

The invention claimed is:

1. A measurement device with a support plate (1) mounted on measurement cells, and with a display device for displaying a force action line (7) for a person standing on bearing surfaces (10, 10') of the support plate (1), wherein lifting devices (9) are arranged underneath the bearing surfaces (10, 10') and above the support plate (1),
    wherein the bearing surfaces (10, 10') are arranged parallel to one another on both sides of a center plane, and
    wherein at least three lifting devices (9) are in each case present on both sides of the center plane.

2. The measurement device as claimed in claim 1, wherein the lifting devices (9) are designed to be steplessly adjustable.

3. The measurement device as claimed in claim 1, wherein the lifting devices (9) are designed to be individually adjustable.

4. The measurement device as claim in claim 1, wherein the lifting devices (9) are designed to be electrically adjustable.

5. The measurement device as claimed in claim 1, wherein the bearing surfaces (10, 10') can be varied by means of the lifting devices (9) in a bearing angle parallel to the center plane.

6. The measurement device as claimed in claim 1, wherein the bearing surfaces (10, 10') can be varied by means of the lifting devices (9) in a bearing angle transverse to the center plane.

7. The measurement device as claimed in claim 1, wherein the lifting devices (9) for the bearing surfaces (10, 10') are arranged symmetrically with respect to the center plane.

8. The measurement device as claimed in claim 1, wherein the lifting devices (9) consist of a central hollow spindle screw (22) in engagement with at least one sleeve part (15, 19) which is rotationally fixed and has an internal thread (17, 21) cooperating with the spindle screw (22).

9. The measurement device as claimed in claim 8, wherein a drive mechanism of the spindle screw (22) is formed with a toothed ring arrangement (27, 28) arranged in the inside of the spindle screw (22) and in engagement with an internal toothing (25) of the spindle screw (22).

10. The measurement device as claim in claim 9, wherein the toothed ring arrangement (27, 28) has a planetary gear configuration.

11. The measurement device as claimed in claim 9, wherein a drive motor of the toothed ring arrangement (27, 28) is also arranged in the inside of the spindle screw (22).

12. The measurement device as claimed in claim 1, wherein the lifting device (9) has upper and lower rotationally fixed sleeve parts (15, 19) which cooperate with oppositely directed external thread sections (23, 24), respectively, of the spindle screw (22).

13. The measurement device as claimed in claim 8, wherein the spindle screw (22) has a diameter of greater than 5 cm.

14. The measurement device as claimed in claim 1, wherein the display of a line of the center of gravity is formed by projection of part of a plane of the center of gravity over the support plate (1).

15. The measurement device as claimed in claim 14, wherein a laser beam (7) oscillating perpendicularly with respect to the support plate (1) is provided in order to project part of the plane of the center of gravity.

16. The measurement device as claimed in claim 14, wherein, in order to project part of the plane of the center of gravity, a light beam is formed linearly by means of a lens optical system.

17. The measurement device as claimed in claim 8, wherein the spindle screw (22) has a diameter of greater than 10 cm.

* * * * *